United States Patent
Deffeyes

(10) Patent No.: US 7,639,006 B2
(45) Date of Patent: Dec. 29, 2009

(54) DETECTOR FOR MAGNETIC HAZARDS TO IMPLANTED MEDICAL DEVICE

(76) Inventor: Kenneth S. Deffeyes, 46 Princeton Ave., Princeton, NJ (US) 08540

(*) Notice: Subject to any disclaimer, the term of this patent is extended or adjusted under 35 U.S.C. 154(b) by 712 days.

(21) Appl. No.: 11/421,865

(22) Filed: Jun. 2, 2006

(65) Prior Publication Data

US 2006/0276850 A1    Dec. 7, 2006

Related U.S. Application Data

(60) Provisional application No. 60/687,480, filed on Jun. 3, 2005.

(51) Int. Cl.
*G01R 33/02* (2006.01)
*A61N 1/02* (2006.01)

(52) U.S. Cl. ............. 324/260; 607/27; 600/11

(58) Field of Classification Search ........ 324/240, 324/249, 260; 607/27, 33; 600/1–3, 9, 11–12; 335/151–152, 205–207
See application file for complete search history.

(56) References Cited

U.S. PATENT DOCUMENTS

| 4,260,949 | A | 4/1981 | Dalton, Jr. |
| 4,622,644 | A | 11/1986 | Hansen |
| 5,128,641 | A | 7/1992 | Posey |
| 6,984,978 | B2 | 1/2006 | Wan et al. |

*Primary Examiner*—Bot L LeDynh
(74) *Attorney, Agent, or Firm*—Fox Rothschild LLP; Richard C. Woodbridge

(57) ABSTRACT

A handheld detector gives a warning when a magnetic field exceeds the safety level for a particular medical implant that is magnetically activated. A front surface of the device corresponds approximately to a surface region of a patient's body in a vicinity of an implanted medical device. The magnetic detection element is located at substantially the same distance from the front surface as the control element of the medical device is from the surface region of the patient's body when the device is implanted. The detector element may be activated by a magnetic pressure, that is the vector cross product of the magnetic flux density (B) of a magnet and the applied magnetic field (H), which is less than the magnetic pressure that activates the control element of the implant device. An electronic circuit connected to the detection element may be used to indicate activation of the detection element.

15 Claims, 4 Drawing Sheets

DETECTOR FOR MAGNETIC HAZARDS TO IMPLANTED MEDICAL DEVICE

CROSS REFERENCE TO RELATED APPLICATIONS

This application claims the priority of U.S. Provisional Application Ser. No. 60/687,480 entitled "Magnetic Sensor for Cerebrospinal Shunt Safety" filed on Jun. 3, 2005 by Kenneth S. Deffeyes, the entire contents and substance of which are hereby incorporated by reference.

FIELD OF THE INVENTION

This invention relates to portable devices to detect magnetic fields, and particularly to portable devices that detect magnetic fields from permanent magnets or DC electromagnets and deliver warnings if the detected magnetic field could affect implanted medical devices.

BACKGROUND OF THE INVENTION

A variety of medical implant devices are designed to be controlled, or modified, by the presence of strong magnetic fields. For example, pacemakers, defibrillators, cerebrospinal shunts, and vagus nerve stimulators are all designed to be controlled or modified by locally applied strong magnetic fields. Persons fitted with such implant devices are warned that exposure to magnetic fields above a certain level can cause unwanted modification of the implant device's function. Such warnings from device manufacturers range from 90 gauss for Medtronic Inc. of Minneapolis, Minn. "Strata" shunt to as little as 5 to 10 gauss for typical pacemakers and defibrillators.

Without a suitable magnetic survey meter, however, a patent fitted with such an implant device has no sense of how strong a particular magnetic field is and, therefore, is best advised to avoid all magnets or magnetic fields. This is not a simple task as such a patent faces potential hazards from an increasing variety of permanent magnets. For instance, cabinet door latches, screwdriver bit holders, electric motors, computer disk drives, badge holders, and audio speakers are just some of the places that permanent magnets having a flux density in excess of 5 gauss may be found. In addition, high-fidelity loudspeakers, audio speakers in telephones, cell phones, head phones and in toys that emit realistic sounds may also have magnetic fields that may pose a problem to such patients. Moreover, the threat is not always obvious. Magnets may also be located in what may appear to the ordinary person to be unlikely places. For instance, beneath some automobile seats there are magnets having flux densities in excess of 5 gauss that close a switch to verify that the seat is occupied. Even a sushi bar conveyor belt may contain magnets that are a problem for persons having a medical implant device.

Conventional magnetometers tend to be expensive, non-portable, and require electric power, making them of limited utility to a patent with a medical implant.

Even with an accurate magnetometer, the results require careful interpretation.

For instance, a major shortcoming of the existing warning system is an incorrect interpretation of the underlying physics involved in the activation of the magnetic switches. Almost all implant manufacturers express their warnings in terms units of "gauss." The gauss (or the Tesla, which is 10,000 gauss) is defined as a magnetic flux density. No mention of a length scale is involved. A magnetic flux density in gauss is roughly the equivalent of saying something is red. It could be a red speck in the eye of a fly, the side of a barn, or Jupiter's Great Red Spot. All are red, but there is no discussion of how much red paint would be needed to give it a second coat. Magnetic flux densities of 1000 to 2000 gauss exist on a small scale in magnetic tapes and credit cards, but because of the tiny size of their magnetic domains, they present no hazard to a medical implant. Similarly, many scientific equipment retailers such as, but not limited to, Radio Shack Corporation of Fort Worth, Tex., sells rare-earth magnets with 10,800 gauss flux densities but the small size (1.5 millimeter thick and 5 millimeter diameter) renders the magnet incapable of reaching a 90 gauss level at a typical depth inside a patient.

SUMMARY OF THE INVENTION

Briefly described, the invention comprises a handheld detector that gives a warning when the magnetic field exceeds the safety level for a particular medical implant. The detector is housed in a casing that corresponds, in part, to the portion of the patent's body containing the medical implant. This allows realistic warnings to be obtained for magnetic fields that pose a real threat, while avoiding undue false positives from magnets or magnetic fields that could not get close enough to the magnetic switches in an actual implant device to cause a problem. The detector may give a warning when a hazardous magnetic field of either polarity in a hazardous orientation is present. The required sensitivity may, for instance, be determined empirically using an actual implant.

In a preferred embodiment a portable, magnetic field detector is calibrated to identify hazards to an implanted medical device having a control element that is magnetically activated. A housing having a front surface corresponding approximately in shape to a surface region of a patient's body in a vicinity of where said medical device may be implanted contains a detection element that is magnetic-field-activated and is located at substantially a same distance from said front surface as the control element of the medical device is from said surface region of the patient's body when the device is implanted. The detector element may be activated by a magnetic pressure that is less than the magnetic pressure that activates the control element of the implant device. An electronic circuit connected to the detection element may be used to indicate activation of the detection element.

In a preferred embodiment, the magnetic pressures are a vector cross product of the magnetic flux density (B) of a magnet and the applied magnetic field (H) intercepted by the control element and the detection element.

In a further preferred embodiment, the implanted control element may be activated by a magnetic field having a particular orientation with respect to the surface region of the patient's body. In such a situation, the detection element may be activated by a magnetic field having substantially the same orientation with respect to the surface of the housing.

In another preferred embodiment of the invention, the detector element may comprise one or more reed switches that may be located orthogonally to each other.

These and other features of the invention will be more fully understood by references to the following drawings.

DETAILED DESCRIPTION

Figure 1A:
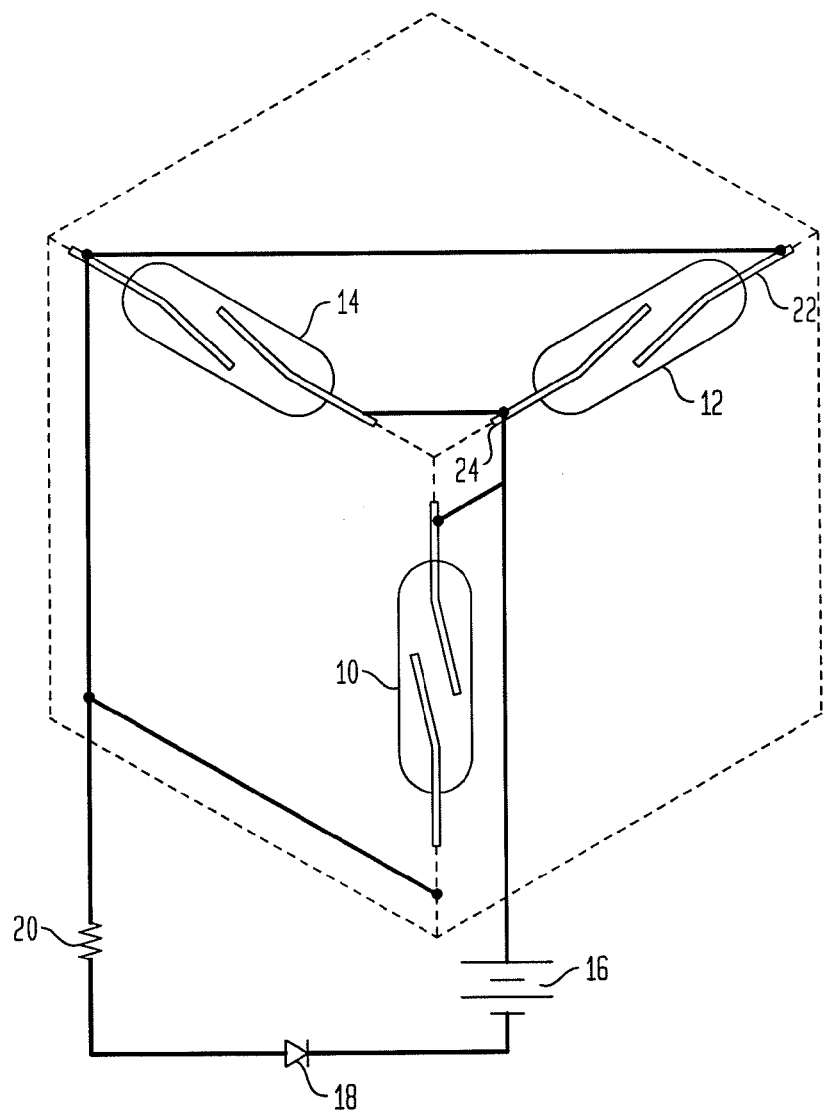
FIG. 1 shows a conventional arrangement of magnetic reed switches connected in electrical parallel oriented in mutually-perpendicular orientation.

The present invention applies to portable devices to detect magnetic fields, and particularly to portable devices that detect magnetic fields from permanent magnets or DC electromagnets that could affect implanted medical devices. Such a device is desirable because a variety of medical implant devices are designed to be controlled, or modified, by the presence of strong magnetic fields.

The implant manufacturer advises the patient, or the caregiver, to avoid magnetic fields stronger than a certain level. Three problems arise:

1. The patient is confronted with a world in which magnets are found in profusion. Toys, loudspeakers, headphones, and refrigerator note holders are just a few examples. Avoiding all magnets is an endless task. A laboratory-grade magnetometer usually costs $1000 or more, is not portable, and has to be plugged into an electric power source. The patient needs a yes-or-no answer about the strength of the magnetic field. A portable, battery-powered, inexpensive magnetometer with a reliable sensitivity level is seriously needed.

2. The strength of the magnetic field is only part of the required answer. The surgical implant is usually sensitive only to certain orientations of the magnetic field. The detector should be sensitive to the hazardous orientations, but should not issue false alarms for safe orientations.

3. Further, there is a length scale involved. The magnetized bits on credit cards and magnetic recording tapes typically have local magnetic flux densities of 1000 gauss, well above the 10 to 90 gauss warnings for medical implants. Yet a credit card is not a hazard because of the tiny scale of the magnetized areas. The hazard sensor should respond to a length scale appropriate to the particular implant.

There are a number of magnetic detectors. Most, however, tend to be large and expensive. The basic types of magnetic sensors include:

1. Hall-effect devices measure the magnetic flux density in gauss (or the SI unit Tesla, which is 10,000 gauss) and are described in detail in, for instance U.S. Pat. No. 4,622,644 granted to Hansen on Nov. 11, 1986 entitled "Magnetic position and orientation measurement system", the contents of which are hereby incorporated by reference. Almost universally, the magnetic flux density has the symbol B in equations. Hall-effect sensors are directional and the response is reversed if the magnetic field is reversed. Although the Hall-effect sensor has been implemented in a chip only a few millimeters in size, the associated power supply and readout is typically bulky and expensive.

2. Magnetoresistive sensors are typically sold as detectors of the applied magnetic field strength H and are described in, for instance, in U.S. Pat. No. 6,984,978 granted to Wan, et al. on Jan. 10, 2006 entitled "Magnetic field sensor", the contents of which are hereby incorporated by reference. In the older CGS system, the unit of magnetic field strength was named the "oersted." In the SI system, the units of H are amperes per meter, but the unit is not given a name. Substances showing large magnetoresistive effects increase their resistance when a magnetic field of either polarity is applied. Elaborate methods, like the "barber pole," are used to bias magnetoresistive detectors to eliminate that inherent symmetry.

3. Reed switches are rated in ampere-turns, although the rating depends on the characteristics of the magnetic coil. Reed switches are described in, for instance, U.S. Pat. No. 5,128,641 granted to Posey on Jul. 7, 1992 entitled "Magnetic switches", the contents of which are hereby incorporated by reference. Manufacturers of reed switches can typically exert only an approximate control over the magnetic field which will close the switch. Some improvement comes from sorting out a batch of as-manufactured switches into closer tolerances, but even after sorting there is typically a 50 percent range in the magnetic field that will close individual switches. Reed switches are frequently used as internal components within pacemakers and defibrillators.

4. MEMS stands for "Micro Electro Mechanical System" that maybe the micromachined equivalent of a reed switch. MEMS tend to be frail, and can unexpectedly stick in the closed position.

5. Proton precession magnetometers measure the total magnetic field, not a directional component of the field and are described in, for instance, U.S. Pat. No. 4,260,949 granted to Dalton, Jr. on Apr. 7, 1981, entitled "Magnetic field detection apparatus", the contents of which are hereby incorporated by reference. In addition to the cost and power, a typical proton precession magnetometer has a one-liter sensor and is not useable in the presence of large magnetic gradients.

6. A flip coil may be used to measure a magnetic field in a straightforward manner that is grounded in electromagnetic theory. As a practical matter, the quantity delivered by the flip coil is in units of electric charge (coulombs). Electrometers sensitive to low levels of coulombs based on flip coils are manufactured by, for instance, Kiethley Instruments of Cleveland, Ohio, but have the disadvantage of costing upwards of a thousand dollars.

7. A torque exerted by a magnetic field on a current-carrying coil has the same theoretical explanation as the flip coil. However, measuring small physical forces is not easy, and is not possible in a hand-held device.

8. Even an ordinary compass may be used as a detector, but the interpretation is almost impossible because of the unknown length of the magnetic dipole of the offending magnet.

A preferred embodiment of the invention will now be described in detail by reference to the accompanying drawings in which, as far as possible, like elements are designated by like numbers.

FIG. 1 shows a three-dimensional arrangement of reed switches. The switches 10, 12, and 14 are commercially available magnetic reed switches. Typically, a reed switch contains two lengths of an electrically conductive metallic alloy which exhibits strong magnetic susceptibility but minimal magnetic remanence, i.e., a magnetically "soft" material. The overlapping ends of the reed switch, which make the electrical contact, are protected inside a sealed glass enclosure. In the drawings, the magnetically soft alloy is identified by a double line. The magnetic leads coming out of the reed switches are preferably not connected to one another to keep the sensors independent of one another. Single lines refer to nonmagnetic electrical wires such as, but not limited to, copper or aluminum wires. A battery or power supply 16, a light-emitting diode 18, and a current-limiting resistor 20 are connected so as to inform the user if one or more of the reed switches is closed, as shown in FIG. 1.

Although reed switches are available in various sizes and sensitivities, the overall length of the magnetically soft wires, as from point 22 to point 24, is important. The protruding ends of the as-manufactured reed switch can be trimmed to the appropriate length. The underlying reason for importance of this length is given in the following paragraph.

The correct physical description of the magnetic hazard faced by a person having a magnetically susceptible implant is not simply the magnetic flux density (B), as many implant manufacture's warning labels appear to indicate. The magnetic hazard is provided by the applied magnetic field, (a.k.a. the "magnetic pressure") that is present on the magnetic switches in the implant device. This magnetic pressure is the product of the magnetic flux density (B) and the applied magnetic field (H). Magnetic flux density, which is usually denoted by B, is typically reported in terms of gauss or Tesla. The applied magnetic field, usually denoted by H, has the units of oersted in the older CGS system. In modern SI units, H does not have a named unit but it reported as "Amperes per meter." One oersted equals 79.578 amperes per meter. What we require is the vector cross product B×H. The product B×H has SI units of newtons per square meter, the same units as pressure. (Because B and H are vectors, the B×H product has a direction. In contrast, fluid pressures are undirected scalars.) The force between two parallel magnet faces is B×H times the area of the magnet faces.

Because the applied magnetic field is important, a length becomes important. The magnetically-responsive element inside any particular medical implant model has a length. It is important that the magnetic length of the reed switch, as from point 22 to point 24 in FIG. 1, be comparable to the magnetic element inside the medical implant. In a preferred embodiment of the invention, the magnetic length of the reed switch is within 20 percent of the length of the magnetic element inside the medical implant, and in a further preferred embodiment, within 10%.

Figure 2:
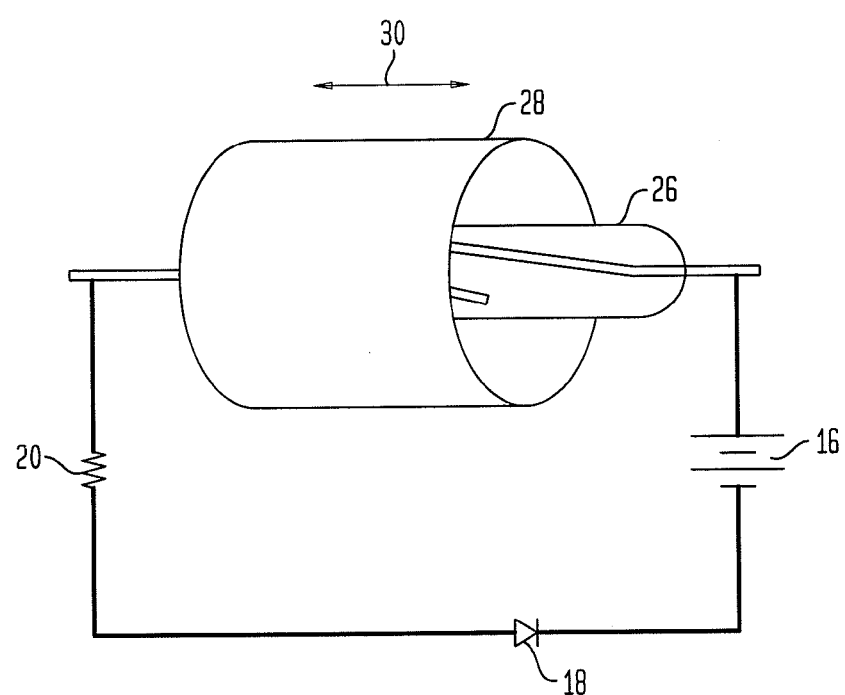
FIG. 2 shows a reed switch, adjusted in sensitivity a magnetically soft shunt.

FIG. 2 shows a single reed switch 26 with its sensitivity adjusted with a magnetically-soft shunt 28. The battery, light-emitting diode, and resistor are shown with the same symbols as numbers 16, 18, and 20 on FIG. 1. Although shunts for reed switches are well known in the art, there are several advantages in using shunted reed switches in this invention. First, there may not be a commercial reed switch available with the appropriate magnetic sensitivity to match a particular medical implant. A more sensitive switch can be utilized with a shunt to lower the sensitivity. Second, the as-manufactured reed switches even in a single batch, typically have magnetic sensitivities than range 50 percent from lowest to highest. Individually-adjusted shunts allow the reed switches to respond at the desired level. Third, most electrical batteries have some magnetic remanence; they act as small permanent magnets. With the batteries in place, the last manufacturing step is sliding the shunt, in the direction of the arrow 30, to the desired sensitivity to an external magnetic field and gluing them in place.

A particularly satisfactory magnetic shunt consists of a rolled-up tube of metallic glass, such as the unannealed 2705M alloy produced by Metglas, Inc. of Conway, S.C.

There is an important distinction between false positive and false negative errors.

A false positive is the device producing a hazard warning when the potentially offending magnet is not strong enough to cause a problem by activating the magnetic switch, or the magnetically operated device, in the implant device. A false positive is a nuisance. The nuisance can be minimized by individually-adjustable reed switches with magnetic shunts. These shunts are used to minimizes how much less the magnetic pressure that activates the magnetic switch in the detector device is than the magnetic pressure that activates the magnetic switch in the implant device.

A false negative is the detection device not responding to a dangerous magnet. A false negative risks a dangerous, even lethal, exposure to a magnetic field. To a avoid a false negative, the warning threshold has to be set a safe distance below the actual hazard level, i.e., the magnetic pressure that activates the magnetic switch in the detector device is made a preset amount less than the magnetic pressure that activates the magnetic switch in the implant device.

In most pacemakers and defibrillators, the magnetically-sensitive element is itself a small reed switch. For those applications, simply replicating the same reed switch inside the hazardous-magnet detector would give no safety factor because of the as-manufactured variations among reed switches of the same design. To provide a safety factor, the detector should contain a more sensitive reed switch, with or without a magnetic shunt.

Figure 3:
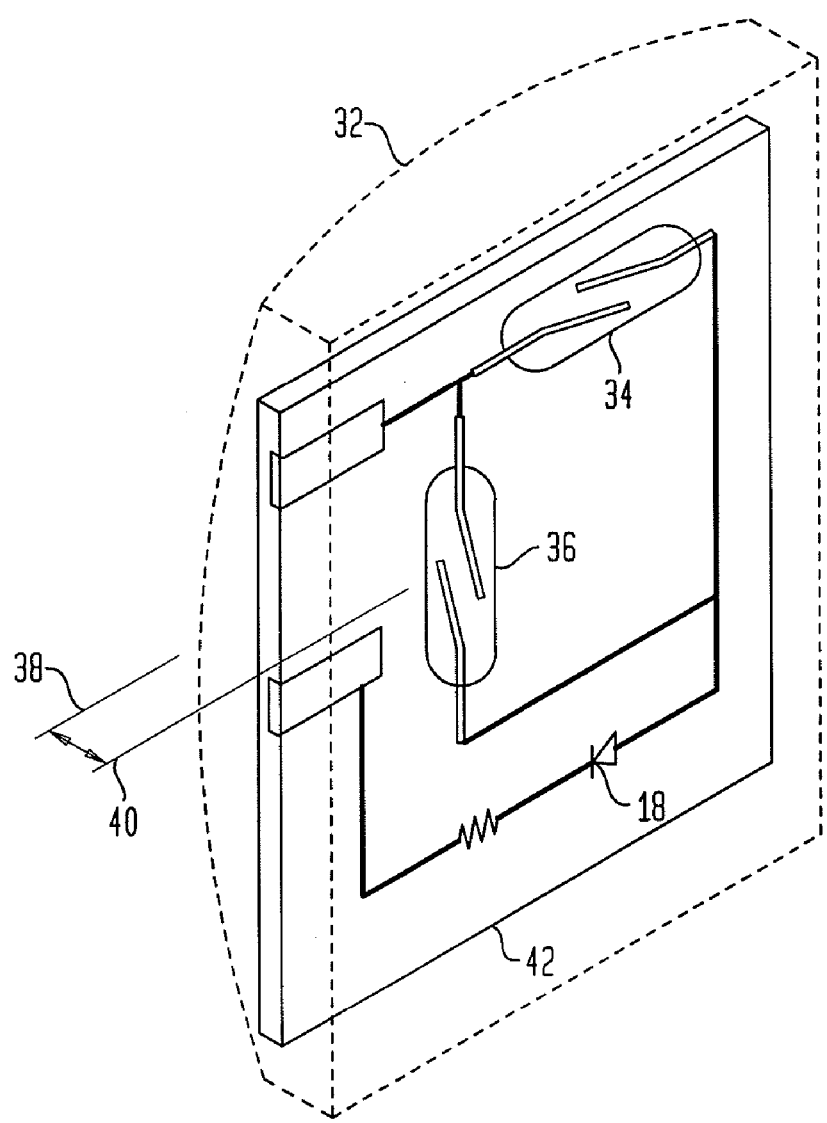
FIG. 3 shows a detector arrangement appropriate to a medical implant sensitive to a single magnetic field orientation.

FIG. 3 shows a preferred embodiment of the present invention. The assembled magnetic detector may be considered, in some respects, to be a synthetic patient. The side of the housing, facing the magnet being tested, has a curved surface 32 with approximately the curvature of the patient's skin above his or her medical implant. The reed switches, 34 and 36, are mounted behind the curved surface at a distance from the curved surface 32 at approximately the depth from the patient's skin to the implant. This depth is typically ten millimeters in adults and 5 millimeters in infants and is shown in FIG. 3 as the distance from line 38 to 40. The reed switches 36 may incorporate magnetically soft shunts, as shown previously in FIG. 2. In, for instance, the Medtronic STRATA cerebrospinal fluid control implant made by Medtronic Inc. of Minneapolis, Minn., and in almost all pacemakers and defibrillators, the magnetic sensitivity of the implant is parallel to the patient's outer skin. Therefore, the long axes of the reed switches, 34 and 36, are parallel to the average direction of the curved face 32, but perpendicular to one another. The reed switches are connected in parallel as a logical OR circuit. If either switch 34 or switch 36 is closed, the Light Emitting Diode (LED) 18 will light up. This allows the user to place the curved surface of the detector against the external surface of an object, such as a toy or a loudspeaker, and the LED will light up for any orientation or any polarity of a potentially hazardous magnetic field. Although FIG. 3 shows a thin, square lithium battery 42, the response would be the same with conventional cylindrical dry cells. The LED and the resistor are the same as 18 and 20 on FIG. 1.

Figure 4:
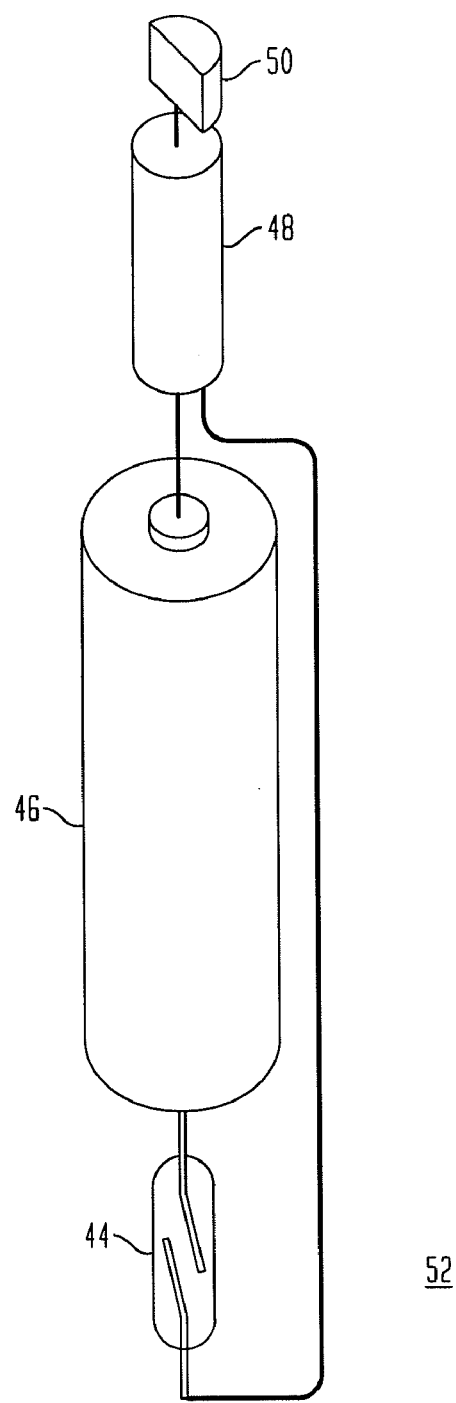
FIG. 4 shows a detector arrangement appropriate for a pacemaker implant device.

FIG. 4 shows a further preferred embodiment of a detector arrangement appropriate for a pacemaker implant device. The proxy pacemaker detector 52 includes a reed switch 44, a dry cell 46, an electric motor 48 and an eccentric weight 50. The proxy pacemaker detector 52 may be housed in container (not shown) suitable for wearing in a breast shirt pocket, such as, but not limited to, a pen shaped housing with a clip, or for being suspended about from a patient's neck, such as, but not limited to, a chain. In this way the reed switch 44 of the proxy pacemaker detector 52 may be positioned close to the actual reed switch of the patient's actual pacemaker implant device. As a typical pacemaker magnetic control element is located approximately one cm beneath an adult patient's skin, and approximately one millimeter beneath an infant patient's skin, the reed switch 44 of the proxy pacemaker detector 52 may be worn to be located substantially in the vicinity of the actual reed switch of the actual pacemaker device, and may be within a distance of 5 cm and easily within a distance of 10 cm. The reed switch 44 of the proxy pacemaker detector 52, however, is set to be significantly more sensitive than the reed switch in the actual pacemaker. As the earth's magnetic field is approximately 0.5 gauss, and pacemaker wearers are warned to avoid magnetic field's of between 5 to 10 gauss, the reed switch 44 of the proxy pacemaker detector 52 may be set to be sensitive to a magnetic field of between 1 and 8 gauss, and preferably in a range of 2 to 4 gauss, dependent on the pacemaker in question. A rough rule of thumb may be a sensitivity that is half the sensitivity of the pacemaker or less, but twice the strength of the ambient earth magnetic field or more.

The reed switch 44 of the proxy pacemaker detector 52 is oriented in approximately the same direction as the reed switch of the actual pacemaker and is of comparable physical size. As the reed switch 44 is set to be more sensitive than the actual reed switch and is of comparable size, it will be activated by a magnetic pressure B×H that is less than the magnetic pressure that will activate the actual reed switch of the pacemaker device. When activated, the reed switch 44 closes, a conduction path is formed that allows the dry cell 46 to power the electric motor 48 with the attached eccentric weight 50. The result is that the wearer of the proxy pacemaker detector 52 is warned by the vibration of the spinning eccentric weight 50. The warned wearer may setback to avoid having their pacemaker reset by the magnetic field. As resetting the pacemaker is not fatal but merely an inconvenience, as it is reset to a default condition, the proxy pacemaker detector 52 does not have to be perfect. The proxy pacemaker detector 52 may, however, provide a level of confidence to a wearer.

One of ordinary skill in the art will readily appreciate that the reed switch 44 of the proxy pacemaker detector 52 may be adjusted in sensitivity using a shunt, as described in detail above in describing FIG. 2.

One of ordinary skill in the art will readily appreciate that the proxy pacemaker detector 52 may have a suitable audio or optical warning signal instead of, or in addition to, the vibration warning system described above.

Alternative Embodiments

Although utilizing a light-emitting diode to report a closed switch is a simple, low-power configuration, any conventional light, sound, or vibration annunciator may be substituted for the light-emitting diode and provide a similar warning functionality, or may be used in conjunction with an LED to augment the warning.

Although any of the magnetically-sensitive detectors described above may be used as the detector element in a safety detector, the high cost, power requirement, and length-matching may make such a solution less desirable than the preferred embodiment presented above. Of the alternatives, the fluxgate magnetometer utilizes a magnetically-sensitive element of a defined length. Standard fluxgate magnetometers measure much weaker fields than the fields hazardous to medical implants, but a less sensitive fluxgate might be developed.

Although every reasonable attempt is made in the accompanying drawings to represent the various elements of the embodiments in relative scale, it is not always possible to do so with the limitations of two-dimensional paper. Accordingly, in order to properly represent the relationships of various features among each other in the depicted embodiments and to properly demonstrate the invention in a reasonably simplified fashion, it is necessary at times to deviate from absolute scale in the attached drawings. However, one of ordinary skill in the art would fully appreciate and acknowledge any such scale deviations as not limiting the enablement of the disclosed embodiments.

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention. Modifications may readily be devised by those ordinarily skilled in the art without departing from the spirit or scope of the present invention.

What is claimed is:

1. A portable, magnetic field detector calibrated to identify hazards to an implanted medical device having a control element that is magnetically activated, said detector comprising:
   a detection element that is magnetic-field-activated and is oriented in substantially the same orientation as said control element of said medical device and wherein said detector element is activated by a first magnetic pressure, and said control element is activated by a second magnetic pressure, and where in said first magnetic pressure is less than said second magnetic pressure by a predetermined amount; and
   a detection indicating circuit connected to said a detection element.

2. The detector of claim 1 wherein said detection element is located substantially in the same location as said control element of said medical device, and wherein said first magnetic pressure is less than or equal to half said second magnetic pressure.

3. The detector of claim 2 wherein said detection indicating circuit includes an electric motor having an attached eccentric weight.

4. The detector of claim 1 further comprising a housing comprising a front surface corresponding approximately in shape to a surface region of a patient's body in a vicinity of where said medical device may be implanted; and wherein said detector element is located at substantially a same distance from said front surface as said control element of said medical device is from said surface region of said patient's body when said device is implanted.

5. The detector of claim 4 wherein said first and second magnetic pressures are a vector cross product of B, the magnetic flux density of a magnet and H the applied magnetic field intercepted by said control element and said detection element.

6. The detector of claim 4 wherein said implanted control element is activated by a first magnetic field having a first orientation with respect to said surface region of said patients body and wherein said detection element is activated by a second magnetic field have substantially said first orientation with respect to said first surface of said housing.

7. The detector of claim 6 wherein said detection element comprises one or more reed switches.

8. The detector of claim 7 wherein said detection element comprises two orthogonal reed switches.

9. The detector of claim 8 wherein both said reed switches are in a plane parallel to said front surface of said housing.

10. The detector of claim 6 wherein said detection element comprises three orthogonal reed switches.

11. The detector of claim 5 further comprising one or more shunts attenuating a magnetic sensitivity of said reed switches.

12. The detector of claim 10 wherein said shunts are comprised of metallic glass.

13. The detector of claim 5 further comprising a battery.

14. The detector of claim 13 further configured to be portable.

15. The detector of claim 14 further configured to be hand-held.

* * * * *